United States Patent [19]

Glaser et al.

[11] Patent Number: 5,767,079
[45] Date of Patent: Jun. 16, 1998

[54] METHOD OF TREATING OPHTHALMIC DISORDERS USING TGF-β

[75] Inventors: Bert M. Glaser, Baltimore, Md.; Bruce B. Pharriss, deceased, late of Palo Alto, Calif., by Joyce A. Pharris, Executrix; Ann F. Hanham, Palo Alto, Calif.; George A. Ksander, Redwood City, Calif.

[73] Assignee: Celtrix Pharmaceuticals, Inc., Santa Clara, Calif.

[21] Appl. No.: 705,694

[22] Filed: Aug. 27, 1996

Related U.S. Application Data

[63] Continuation-in-part of Ser. No. 423,412, Apr. 18, 1995, abandoned, which is a continuation of Ser. No. 88,886, Jul. 8, 1993, abandoned, which is a continuation-in-part of Ser. No. 8,778, Jan. 22, 1993, abandoned, which is a continuation-in-part of Ser. No. 910,834, Jul. 8, 1992, abandoned.

[51] Int. Cl.$^6$ .................................................. A61K 38/18
[52] U.S. Cl. ............................ 514/12; 514/21; 530/399
[58] Field of Search ........................ 514/12, 21; 530/399

[56] References Cited

U.S. PATENT DOCUMENTS

| | | | |
|---|---|---|---|
| 4,774,322 | 9/1988 | Seyedin et al. | 530/353 |
| 4,939,135 | 7/1990 | Robertson et al. | 514/179 |
| 4,983,580 | 1/1991 | Gibson | 514/2 |
| 5,008,240 | 4/1991 | Bentz et al. | 514/2 |
| 5,108,989 | 4/1992 | Amento et al. | 514/12 |
| 5,411,940 | 5/1995 | Nixon et al. | 514/12 |

FOREIGN PATENT DOCUMENTS

WO 92/02247  2/1992  WIPO.

OTHER PUBLICATIONS

Gass, "Idiopathic senile macular hole—its early stages and pathogenesis" *Arch. Ophthalmol.* (1988) 108:629–639.
Feeny–Burns et al., "Aging human RPE: morphometric analysis of macular, equatorial, and peripheral cells" *Invest. Ophthamol. Mol. Vis. Sci.* (1984) 25:195–200.
MPS Group, "Laser photocoagulation of subfoveal neovascular lesions in age–related macular degeneration" *Arch. Ophthalmol.* (1991) 109:1220–1231.
MPS Group, "Laser photocoagulation of subfoveal recurrent neovascular lesions in age–related macular degeneration" *Arch. Opthalmol.* (1991) 109:1232–1241.
MPS Group, "Subfoveal neovascular lesions in age–related macular degeneration" *Arch. Opthalmol.* (1991) 109:1242–1257.
Sebag et al., "Diabetic retinopathy. Pathogenesis and the role of retina–derived growth factor in angiogenesis" *Survey Ophthamol.* (1986) 30:377–384.
Wiedemann, "Growth factors in retinal diseases: proliferative vitreoretinopathy, proliferative diabetic retinopathy, and retinal diseases: proliferative vitreoretinopathy, proliferative diabetic retinopathy, and retinal degeneration" *Survey of Ophthalmol.* (1992) 36(5):373–384.

Berritault et al., "Is there a ubiquitous growth factor in the eye?" *Differentiation* (1981) 18:29–42.
Chen et al., "Angiogenic activity of vitreous and retinal extract" *Invest. Ophthamol. Vis. Res.* (1980) 19:596–602.
D'Amore et al., "Endothelial cell mitogens derived from retina and hypothalamus: biochemical and biological similarities" *J. Cell Physiol.* (1984) 99:1545–1549.
Elstow et al., "Bovine retinal angiogenesis factor is a small molecule (molecular mass<600)" *Invest. Ophthamol. Vis. Sci.* (1985) 26:74–79.
Glaser et al., "The demonstration of angiogenic activity from ocular tissues" *Ophthamol.* (1980) 87:440–446.
Ruelius–Altemose e al., "Vascular endothelial cell growth: inhibition vs. stimulation" *Invest. Ophthamol. Vis. Sci.* (1985) 26(ARVO Suppl.):25.
Langer et al., "Isolation of a cartilage factor that inhibits tumor neovascularization" *Science* (1976) 193:70–71.
Raymond et al., "Isolation and identification of stimulatory and inhibitory cell growth factors in bovine vitreous" *Exp. Eye Res.* (1982) 34:267–286.
Lane et al., "Sjögren's syndrome" *Harrison's Principles of Internal Medicine* 12th Edition, McGraw–Hill Publishers, (1991) pp. 1449–1550.
Chiefetz et al., "The transforming growth factor–J system, a complex pattern of cross–reactive ligands and receptors" *Cell* (1987) 48:408–415.
Ikeda et al., "Human transforming growth factor type J2: production by a prostatic adenocarcinoma cell line, purification, and initial characterization" *Biochem.* (1987) 26:2406–2410.
Seyedin et al., "Cartilage–inducing factor–B is a unique protein structurally and functionally related to transforming growth factor–J" *J. Biol. Chem.* (1987) 262:1946–1949.
Derynck et al., "A new type of transforming growth factor–J, TGF–J3" *EMBO J.* (1987) 7(12):3737–3743.
Madisen et al., "Transforming growth factor–J2: cDNA cloning and sequence analysis" *DNA* (1988) 7(1):1–8.
Smiddy et al., "Transforming growth factor–J—a biological chorioretinal glue" *Arch. Ophthalmol.* (1989) 107:577–580.
Ignotz et al., "Transforming growth factor–J stimulates the expression of fibronectin in collagen and their incorporation into the extracellular matrix" *J. Biol. Chem.* (1986) 261(9):4337–4345.
Leschey et al., "Growth factor responsiveness of human retinal pigment eptithelial cells" *Invest. Ophthamol. Vis. Sci.* (1990) 31:839–846.

(List continued on next page.)

*Primary Examiner*—Chhaya D. Sayala
*Attorney, Agent, or Firm*—Morrison & Foerster LLP

[57] ABSTRACT

This invention is a method for the treatment of ophthalmic disorders. The method is suitable for treatment of a variety of disorders including macular holes, macular degeneration, and retinal detachment and tears, cataracts, and corneal and scleral injuries. The method entails application of an effective amount of Transforming Growth Factor-β (TGF-β) to the affected region.

48 Claims, No Drawings

OTHER PUBLICATIONS

Plouët et al., "Transforming growth factor J–1 positively modulates the bioactivity of fibroblast growth factor on corneal endothelial cells" *J. Cell Physiol.* (1989) 141:392–399.

Connor et al., "Correlation of fibrosis and transforming growth factor–J type 2 levels in the eye" *J. Clin. Invest.* (1989) 83:1661–1666.

Ryan, S.J., Editor in Chief, *Retina* (1989) The C.V. Mosby Company, St. Louis, Judson, P.H., et al., "Macular Hole" Chapter 68, pp. 229–241.

LaVail, M.M. et al., Editors, *Retinal Degeneration: Experimental and Clinical Studies* (1985) Alan R. Liss, Inc., pp. 389–400.

Newsome, D.A., Editor, *Retinal Dystrophies and Degenerations* (1988) Raven Press, New York, Lewis, R.A., "Juvenile Heredity Macular Dystrophies" Chapter 8, p. 115.

Graycar et al., "Human transforming growth factor–J3: recombinant expression, purification, and biological activities in comparison with transforming growth factors–J1 and –J2" *Molecular Endocrinology* (1989) 3(12):1977–1986.

Lynch et al., "Growth factors in wound healing: single and synergistic effects on partial thickness porcine skin wounds" *J. Clin. Invest.* (1989) 84:640–646.

Glaser et al., "Transforming growth factor–J2 for the treatment of full–thickness macular holes" Paper presented in Oct. 1991, at the American Academy of Ophthalmology Annual Meeting, Anaheim, CA, pp. 1162–1173.

Glaser et al., "Induction of a 'retinal patch' by transforming growth factor–J in the treatment of full thickness macular holes" *Invest. Opthalmol. Vis. Sci.* (1991) 32(4):713 (abstract No. 237).

Roberts, A.B. et al., "Peptide growth factors and their receptors I" Springer Verlag, Sporn et al., eds. Chapter 8, (1990).

Jampel et al., "Transforming growth factor–$\beta$ in human aqueous humor" *Current Eye Research* (1990) 9:963–970.

Tripathi et al., "Role of growth factors in the uveal tract of the eye as targeted to the development of new drugs" *Drug Development Research* (1991) 23:1–25.

ns. 5,767,079

METHOD OF TREATING OPHTHALMIC DISORDERS USING TGF-β

CROSS-REFERENCE TO RELATED APPLICATIONS

This application is a continuation-in-part of U.S. patent application Ser. No. 08/423,412, filed Apr. 18, 1995, which is a continuation of U.S. patent application Ser. No. 08/088,886, filed Jul. 8, 1993, now both abandoned, which is a continuation-in-part of U.S. patent application Ser. No. 08/008,778, filed Jan. 22, 1993, now abandoned, which is a continuation-in-part of U.S. patent application Ser. No. 07/910,834 filed Jul. 8, 1992, abandoned.

FIELD OF THE INVENTION

This invention is a method for treating a variety of ophthalmic disorders in which wound healing is impaired or requires modulation, including macular holes, macular degeneration, retinal detachment and tears, retinal edema, retinal vascular disorders, retinal neovascularization, wound healing disorders, proliferative disorders, anti-degenerative disorders, anti-angiogenesis disorders, dry eye syndromes, uveitis, secondary cataracts, corneal epithelial wounds, corneal neovascularization, Sjögren's syndrome, and surgical wounds. The method entails application of Transforming Growth Factory (TGF-β) to the affected region. TGF-β2 is the preferred form of TGF-β. Other growth factors which have wound healing and neurotrophic effects may also be applied.

BACKGROUND OF THE INVENTION

Major ophthalmic disorders affect the retina, lens and cornea. Among the most important retinal disorders are macular holes and degeneration, retinal tears, diabetic retinopathy, and miscellaneous disorders. The most important disorders of the lens are cataracts and refractive errors. The most important disorders of the cornea are those related to corneal defects, including corneal ulcers and wounds and the consequences of dry eye /Sjögren's syndrome. These are discussed briefly below.

Retinal Physiology

The retina is the light-sensitive portion of the eye. Supported by the choroid and retinal pigment cells and found at the posterior of the eye, the retina contains the cones and rods which detect colors. When the rods and cones are excited, they transmit signals which pass through successive neurons in the retina to the optic nerve and finally to the cerebral center, where a "visual picture" is integrated.

In the center of the retina is the macula lutea, which is about ⅓ to ½ cm in diameter. The macula provides detailed vision, particularly in the center (the fovea), because the cones are higher in density. Blood vessels, ganglion cells, inner nuclear layer and cells, and the plexiform layers are all displaced to one side (rather than resting above the cones), thereby allowing light a more direct path to the cones.

Under the retina are the choroid, a collection of blood vessels embedded within a fibrous tissue, and the deeply pigmented epithelium, which overlays the choroid layer. The choroidal blood vessels provide nutrition to the retina (particularly its visual cells).

Retinal Disorders

There are a variety of retinal disorders, whose current treatment is not optimal. The retina may tear, form holes and separate from the underlying choroid. Of particular concern are macular holes which produce blurred central vision or metamorphopsia. The cause of most macular holes is unknown. However, trauma, cystic degeneration, and vitreoretinal traction have all been associated with hole formation. Full thickness macular holes also appear following myopic degeneration, laser photocoagulation, lightning strike and pilocarpine administration. There also is a higher frequency of macular holes after cataract extraction.

The idiopathic senile macular hole is a disorder occurring generally in healthy women who are in their sixth decade of life or beyond. The more severe holes involve the full thickness of the macula and are surrounded by a halo of retinal detachment. In the early stage, there may be a sudden decrease or distortion in vision. But early changes are difficult for physicians to spot. Patients may experience sudden vision changes or may not notice symptoms if the condition slowly evolves. Some experts believe that macular holes begin with central or foveolar detachment, which eventually develops into a full-depth macular hole. See, Gass, "Idiopathic Senile Macular Hole—Its Early Stages and Pathogenesis", Arch. Ophthalmol. (1988) 108:629–639. Partial holes, that is, holes which are partial in depth or shape, having a new moon or horseshoe shape, are worth diagnosing early, particularly if an effective way to stop progression to macular holes were available.

For macular holes of unknown origin, certain operations, such as transpars plana vitrectomy, may interrupt the progress of macular degeneration toward full-thickness hole formation. However, the surgery may permanently damage central vision. Current methods for treating macular holes improve vision in only 40% of eyes.

Other retinal vascular and macular diseases which may exhibit voids, tears, or separations in the retina resulting from lack of fibrous or supporting tissue.

Macular Degeneration

Age-related macular degeneration (AMD) is the major cause of severe visual loss in United States citizens over the age of 55. Most AMD patients have a build up of deposits within and under the retinal pigment epithelium in the macular region resulting in atrophy of the retina and the retinal pigment epithelium. The retinal pigment cells are long-lived. They scavenge for photoreceptor discs from the rods and cones for years and accumulate intracellular wastes. The incompletely digested residues reduce cytoplasmic space (Feeny-Burns, L. et al., Invest. Ophthal. Mol. Vis. Sci. (1984) 25:195–200) and interfere with metabolism. As the cell volume available to the organelles diminishes, the capacity to digest photoreceptors decreases, and this may be the basis for macular degeneration.

Some patients also experience exudative AMD with choroidal neovascularization, detachment and tears of the retinal pigment epithelium, fibrovascular scarring, and vitreous hemorrhage. This process is responsible for more than 80% of cases of significant visual loss in patients with AMD.

Age-related macular degeneration (AMD) is a sight-threatening disorder which occurs in either an atrophic or (less commonly) an exudative form. In exudative AMD, blood vessels grow from the choriocapillaris through defects in Bruch's membrane, and in some cases the underlying retinal pigment epithelium (RPE). Organization of serous or hemorrhagic exudates escaping from these vessels results in fibrous scarring of the macular region with attendant degeneration of the neuroretina and permanent loss of central vision.

Several studies have recently described the use of laser photocoagulation in the treatment of initial or recurrent neovascular lesions associated with AMD (Macular Photocoagulation Study Group (1991) Arch. Ophthal. 109:1220; Macular Photocoagulation Study Group (1991) Arch. Ophthal. 109:1232; Macular Photocoagulation Study Group (1991) Arch. Ophthal. 109:1242. Unfortunately, AMD patients with subfoveal lesions subjected to laser treatment experienced a rather precipitous reduction in visual acuity (mean 3 lines) at 3 months follow-up. Moreover, at two years post-treatment treated eyes had only marginally better visual acuity than their untreated counterparts (means of 20/320 and 20/400, respectively). Another drawback of the procedure is that vision after surgery is immediately worse.
Retinal Tears The retina may tear or separate from the choroid, and the choroid may rupture, for a wide variety of reasons.

Other situations in which tissue separation is observed include such widely disparate conditions as detachment of retina and pigment epithelium, degenerative myopia, as may be evidenced by visible breaks in Bruch's membrane (lacquer cracks), acute retinal necrosis syndrome (ARN), and traumatic chorioretinopathies or contusion (Purtscher's Retinopathy).
Other Retinal Disorders Other retinal disorders include edema and ischemic conditions. Macular and retinal edema are often associated with metabolic illnesses such as diabetes mellitus. Retinal edema is found in a large percentage of individuals who have undergone cataract extraction and other surgical procedures upon the eye. Edema is also found with accelerated or malignant hypertension. Macular edema is a common complication of prolonged inflammation via uveitis, Eales disease, or other diseases. Local edema is associated with multiple cytoid bodies ("cotton bodies") as a result of AIDS.

Retinal ischemia can occur from either choroidal or retinal vascular diseases, such as central or branch retinal vein occlusion, collagen vascular diseases and thrombocytopenic purpura. Retinal vasculitis and occlusion is seen with Eales disease and systemic lupus erythematosus.
Proliferative Diabetic Retinopathy (PDR)

Sebag and McMeel reviewed the pathogenesis of PDR (Survey of Ophthalmol. (1986) 30:377–84. The initiating event may be inadequate tissue oxygenation which causes vasodilation. Inadequate oxygenation may occur after the arterial basement membrane has thickened with diabetes-related deposits and because of endothelial cell proliferation, which is associated with pericyte degeneration. Basement membrane thickening and loss of pericytes are believed to result from low insulin and hyperglycemia, two important metabolic abnormalities of diabetes.

The neovascularization of PDR has been attributed to the subtle vascular abnormalities described above. Even this slight disruption may permit normally absent chemicals to enter the eye across the blood-retinal barrier.

Several growth factors besides TGF-β appear to be involved in diabetic retinopathy, including fibroblast growth factors (FGF), an interplay of FGF and TGF-β, tumor necrosis factor (TNF-α and β), which are known to have angiogenic properties. (Wiedemann, Survey of Ophthalmol. (1992) 36:373–84). Others have proposed that because retinal blood vessels appear to have a unique response to diabetic ischemia, there may be specific retina-derived growth factors. Berritault et al. Differentiation (1981) 18:29–42; Chen and Chen Invest. Ophthalmol. Vis. Sci. (1980) 19: 596–02; D's Amore and Klagsburn J. Cell. Biol. (1984) 99: 1545–49; Elstow et al. Invest. Ophthalmol. Vis. Sci. (1985) 26:74–79; Glaser et al. Ophthalmology (1980) 87:440–46; and Ruelius-Altemose et al. Invest. Ophthalmol. Vis. Sci. (1985) 26 (ARVO Suppl):25.

Potential inhibitors of retinal angiogenesis have been sought. Tumor-induced angiogenesis was prevented with an extract of cartilage, which weighed about 16,000 daltons and inhibited protease activity. Langer et al. Science (1976) 193:70–71. Later studies indicated that normal vitreous humor contained such an inhibitor. For example, a vitreous protein with a molecular weight of 6200 was found to inhibit RDGF-induced proliferation and thymidine incorporation by vascular endothelial cells in vitro. Raymond and Jacobson, Exp. Eye Res. (1982) 34:267–86.

Clinically, the appearance of cotton wool spots in the retina signifies the onset of retinal ischemia. Sebag and McMeel, ibid. These spots are irregular patches of fibrous tissue.
Uveitis Uveitis refers to inflammation of the uveal tract. It includes iritis, cyclitis and iridocyclitis and choroiditis and usually occurs with inflammation of additional structures of the eye. These disorder has a variety of causes but is typically treated with systemic steroids, topical steroids or cyclosporin. The disease frequently presents with a chronic inflammation occurring either in the anterior segment (70%) or in the posterior segment (30%) which is complicated by episodes of severe exacerbation that may not be controllable with conventional medications. Reports in the literature suggest that 30,000 individuals become legally blind each year in the United States from uveitis. In addition, an estimated 20,000 individuals suffer significant loss of visual acuity from this disorder. Additional means to control this condition, without suppressing infection fighting abilities with steroids, would be highly beneficial.
Cataracts Cataracts are opacities in what should be perfectly clear lenses. Cataracts interfere with the vision by causing blurred vision, glare, altered color perception and monocular diplopia. They are related to a variety of factors, including x-ray exposure and metabolic diseases such as diabetes, Wilson's disease (copper accumulation) and galactosemia. Cataracts are also a side effect of cortisone, methotrexate and nitrogen mustard therapy.
Corneal Epithelial Wounds The cornea and conjunctiva are vulnerable to damage from pathogenic agents or direct trauma, drying associated with disorders of tearing, exposure to radiant energy (ultraviolet light, sun and welding guns), allergens such as pollen and mold, and infectious agents. Keratoconjunctivitis can also occur in patients with Stevens-Johnson syndrome, Wegener's granulomatosis, rheumatoid arthritis, atopic dermatitis and cicatricial pemphigoid. Corneal ulcers may occur.

After corneal surgery, the cornea must heal. Popular types of corneal surgery include cataract extraction, with or without lens replacement; corneal transplants, to treat viral infection or penetrating keratoplasty (PKP); glaucoma filtration surgery; and radial keratotomy and other types of surgery to correct refraction.

Cataract incisions are full thickness wounds in the cornea which are as large as 8 mm in length with conventional intraocular lenses (IOLs) and as small as 3 mm or less with foldable silicone IOLs. These wounds typically heal without difficulty, although they take several months to stabilize and are associated with warpage of the corneal tissues leading to permanent astigmatism. Treatment which could speed stabilization of vision and avoid astigmatism would be highly desirable.

Penetrating keratoplasty (PKP) and corneal transplant are characterized by full-thickness wounds around the entire circumference of the cornea. These wounds tend to remain weak for one or more years. Patients experience drift in visual acuity and increasing risk of wound dehiscence and/or endophthalmitis. It would be highly desirable to stabilize visual acuity and accelerate wound maturation as early as possible, to avoid sight-threatening adverse effects.

Radial keratotomy (RK) is the most widespread technique for altering the shape of the cornea. The most commonly used form of RK is based on the placement of 4–8 surgical incisions in a radial pattern across the cornea. These incisions are typically 70–80% of the depth of the cornea, and are therefore non-penetrating wounds. New laser and mechanical methods of altering the corneal curvature are emerging, with the wound healing issues being a major hurdle that has limited the development and clinical application of these techniques.

Normally, the cornea heals rapidly. FGF is known to be involved in the proliferation of corneal epithelial cells and scleral fibroblasts. TGF-$\beta$ is believed to encourage fetal scleral development but effects later in life have not been reported.

A method of enhancing healing of corneal epithelial wounds without scarring would help maintain vision after the cornea is wounded. Such predictable healing would be highly beneficial in contributing to a more predictable surgical outcome in RK.

Sjögren's Syndrome

Sjögren's syndrome is an immune system disorder which manifests itself in the eyes as conjunctival and corneal dryness (keratoconjunctivitis sicca syndrome) and a gritty sensation in the eyes. This is due to lack of tear resulting from destruction of the lacrimal (or tear) glands by progressive mononuclear cell infiltrate and scarring of the gland. If the cornea is too dry, corneal ulcerations can develop.

"There is currently no effective treatment for the ongoing exocrine gland destruction. Treatment is geared toward symptomatic relief of mucosal dryness . . . and includes artificial tears [and] ophthalmologic lubricating ointments." *Harrison's Principles of Internal Medicine*, 12th ed., McGraw-Hill, pages 1449–50, 1991.

Neovascularization

Neovascularization is a serious complication of a large variety of ocular disorders affecting the various tissues of the eye because it can lead to blindness. Corneal neovascularization occurs in many conditions and diseases, including trauma, chemical burns and corneal transplantation.

Corneal transplantation is successful in many patients because of the absence of blood vessels in the corneal tissue. Because there are no blood vessels in the cornea, the circulating components of the immune system are not exposed to the new cornea and there is normally no problem of host-graft rejection. Induction of neovascularization in the cornea would expose the cornea to the immune system and lead to graft rejection. In addition, a subsequent graft is less likely to be successful, too. Treatments of these various causes of neovascularization may include the administration of immunosuppressives to modulate the inflammatory process, including neovascularization. However, immunosuppressives may inhibit appropriate wound healing in the cornea and interfere with the ability to fight infections. Delayed wound healing leaves the cornea vulnerable to infections for longer periods. Hence, vision-threatening infections can result from current treatments.

Neovascularization of the iris, and its attendant scarring can result in glaucoma and blindness. Neovascularization of this portion of the eye can arise as a consequence of diabetic retinopathy, venous occlusion, ocular tumors and retinal detachment. Most commonly, laser treatment to cauterize the blood vessels is tried; however, that has the attendant risk of causing additional scarring.

Retinal and intravitreal neovascularization occurs in a wide range of disorders including diabetic retinopathy, vein occlusions, sickle cell retinopathy, retinopathy of prematurity, retinal detachment, ocular ischemia and trauma.

Subretinal pigment epithelial (RPE) and sub-retinal neovascularization are common, yet very severe, disorders of the eye. The growth of new blood vessels interferes with the normal anatomy of the visual and pigmentary cells in the eye, leading to severe visual loss. The new blood vessels leak fluid and blood under the macula causing marked distortion and loss of vision. When these blood vessels develop in the avascular foveal region of the eye, the result is central visual loss and legal blindness.

The specific causes of this type of neovascularization are unknown; however, this disease most often affects patients over the age of 50 years old, who may or may not have a family history of subfoveal neovascularization. The visual loss is usually sufficient to result in legal blindness. These is no proven treatment once the blood vessels invade the foveal region. In fact, there are few warning signs that a patient is developing this disorder and there are no preventative measures. Even under close monitoring by an ophthalmologist, patients with subfoveal neovascularization have a poor prognosis. In eyes in which a natural history course is followed with no treatment, visual acuity tends to decrease gradually to a mean of 20/400 (Macular Photocoagulation Study Group, 1991). Alternatively, in eyes treated with macular photocoagulation, visual acuity measurements after one year of laser treatment yielded a mean visual acuity of only 20/320 (Macular Photocoagulation Study Group, 1991). Effective therapy of sub-retinal neovascularization is needed to save vision.

Choroidal neovascularization is caused by such retinal disorders as age-related macular degeneration, presumed ocular histoplasmosis syndrome, myopic degeneration, angioid streaks and ocular trauma. Macular degeneration was discussed above. Choroidal neovascularization has proven recalcitrant to treatment in most cases. In only 10% of cases can laser photocoagulation be attempted. There is no other treatment available. Even with successful laser photocoagulation, neovascularization recurs in about 60–70% of eyes.

Growth Factors

The family of peptides known as TGF-$\beta$ can both regulate cell growth and differentiation. These polypeptides can both stimulate and inhibit cell proliferation depending largely on the cell type and environment. TGFs of some type have been found in almost all tissues from all species of animals which have been examined so far.

TGF-$\beta$2 is a well-characterized material. As noted above, it is a polypeptide and has a molecular weight of about 25,000 D and is a dimer composed of two 12,500 D subunits which are linked by a disulfide (Chiefetz et al., *Cell* (1987) 48:408–415; Ikeda et al., *Biochemistry* (1987) 26:2406–2410) and has been isolated from bovine demineralized bone (Seyedin et al., *J. Biol. Chem.* (1987) 262:1946–1949), porcine platelets (Cheifetz et al., *Cell* (1987) 48:409–415), human prostatic adenocarcinoma cell line, PC-3 (Ikeda et al., 1987, *Biochemistry* 26:2406–2410), etc. Methods for separating and purifying TGF-$\beta$2 are given in U.S. Pat. 4,774,322 to Seyedin et al. TGF-$\beta$1 and TGF-$\beta$2 are found in many of the same cells. However, their mature sequences have only about 75–80% homology (Derynck et al., *EMBO J.* (1987) 7: 3737–3743). It has been established that the several species of TGF-$\beta$ are coded for by different genes. (Madisen et al., *DNA* (1988) 7: 1–8)

It has been observed that TGF-$\beta$ (only TGF-$\beta$1 is mentioned in the article's materials section) appeared to seal the edge of surgical retinotomy in rabbits (See, Smiddy et al., "Transforming Growth Factor-β—A Biologic Chorioretinal Glue", *Arch. Ophthal. Mol.* (1989) 107:577–580). Smiddy et al. showed the formation of fibrotic tissue around the retinotomy which sealed the retina to the choroid layer.

TGF-β2 has been found to stimulate collagen glycoprotein synthesis as well as cellular proliferation and migration involved in the wound healing process. See, Ignotz, "Transforming Growth Factory-β Stimulates the Expression of Fibronectin in Collagen and their Incorporation into the Extracellular Matrix", *J. Biol. Chem.* (1986) 261:4337–45.

TGF-β has been found to inhibit [$^3$H]thymidine incorporation by retinal pigment epithelial cells which is stimulated by platelet-derived growth factor, a-FGF, b-FGF and EGF. According to Leschey, this could be due to TGF-β being linked to a strong inhibitory pathway capable of overriding stimulatory signals from other growth factors. Leschey et al., *Invest. Ophthalmol. Vis. Sci.* (1990) 31:839–46.

In contrast, TGF-β positively modulates the bioactivity of FGF in corneal endothelial cells. Plouet et al., *J. Cell. Physiol.* (1989) 141:392–99.

None of these documents discloses the application of TGF-β to retinal disorders with the result of healing and the improvement of sight.

SUMMARY OF THE INVENTION

This invention is a method of significantly improving the ocular vision in retinal disorders of the mammalian eye, in which the retinal disorders are characterized by a loss or impending loss of fibrous tissue, and in which the method comprises administering to the mammal about 1 to 10 μg of TGF-β. Preferably, the type of TGF-β is TGF-β2.

A further aspect of the invention is that TGF-β is administered by intraocular, subretinal, subscleral, intrascleral, intrachoroidal and subconjunctival injection or by topical, oral or parenteral modes of administration.

In another embodiment of the above invention, the method comprises two additional preceding steps: removing the vitreous humor from the eye; and peeling the epiretinal membrane, if present, from the retina. In this method, TGF-β is administered in an effective amount as a concentrated solution by cannula to the portion of the retina requiring treatment.

In a more preferred embodiment, the retinal disorder to be treated is a macular hole.

In another embodiment, there is provided a method of maintaining or improving the ocular vision in macular degeneration. The method calls for administering to the mammal an amount of TGF-β effective to stabilize or improve vision.

In yet another embodiment, there is provided a method of maintaining or improving the ocular vision in cystoid macular edema. The method calls for administering to the mammal an amount of TGF-β effective to stabilize or improve vision.

In yet another embodiment, the method of treating retinal disorders, which are characterized by decreased connective or fibrous tissue, comprises the steps of removing the vitreous humor from the eye; removing the epiretinal membrane, if present, from the eye; and administering a concentrated solution of TGF-β by cannula to place the TGF-β solution immediately over the portion of the retina requiring treatment.

In accordance with another embodiment of the present invention, there is provided a method for treating an individual with an ophthalmic disorder or poor healing in the eye which can benefit from the administration of TGF-β orally, topically or systemically to an individual in need of such treatment. TGF-β is administered in an amount sufficient to improve healing.

In accordance with a further embodiment of the present invention, the ocular disorder is selected from the group consisting of retinal and corneal wounds, macular degeneration, secondary cataracts, corneal disease and dry eye/Sjögren's syndrome. In a further embodiment, TGF-β is administered by intraocular injection or by application to the cornea. TGF-β can be applied to the cornea by means of eyedrops or a timed release capsule placed in the cul de sac.

. In yet another embodiment, the method provides for administration of TGF-β in an amount sufficient to promote healing and reduce symptoms associated with poor healing. In a further embodiment, the amount of TGF-β administered is at least about 0.5 to 50 μg of TGF-β per treated eye.

In another embodiment, there is provided a method for treating a mammal who has undergone or is about to undergo or is undergoing ophthalmic surgery to promote healing without excessive scarring, said method comprising administering to said mammal TGF-β in an amount sufficient to promote healing without excessive scarring.

The ophthalmic surgery can be, but is not limited to, cataract extraction, with or without lens replacement; corneal transplants, to treat viral infection or penetrating keratoplasty (PKP); glaucoma filtration surgery; and radial keratotomy and other types of surgery to correct refraction.

In another embodiment, there is provided a method for treating a mammal for ocular neovascularization, said method comprising administering to a mammal an effective amount of recombinant human TGF-β2.

In another embodiment, there is provided a method for treating a mammal for uveitis, in which the method comprises injecting an effective amount of TGF-β intraocularly.

While not wishing to be bound by any particular theory, the Inventors propose that the administered TGF-β aids healing by modulating a fibrotic response in the ocular tissues. We have also found that application of an effective dose of TGF-β to the retina appears to provide positive neural regenerative effects as evidenced by the fact that such TGF-β application significantly improves the eyesight of the individuals having the macular holes.

DETAILED DESCRIPTION OF THE INVENTION

The method of this invention is suitable for the treatment of ophthalmic disorders, particularly retinal disorders involving macular degeneration, neovascularization, holes, separations, tears, and the like in the retina or between the retina and its underlying choroidal tissue, or involving choroidal tissue, as described above.

Definitions

"Ophthalmic disorder" refers to physiologic abnormalities of the eye. They may involve the retina, the vitreous humor, lens, cornea, sclera or other portions of the eye, or physiologic abnormalities which adversely affect the eye, such as inadequate tear production.

"Retinal wounds" include, but are not limited to, tears and holes in the retina and separation from the underlying choroid. Retinal wounds appear after trauma, cystic degeneration, vitreoretinal traction, myopic degeneration, laser photocoagulation, lightning strike, pilocarpine administration and cataract extraction. To help the retina heal in a modulated process, TGF-β can be administered.

"Macular degeneration" is characterized by the excessive buildup of fibrous deposits in the macula and retina and the atrophy of the retinal pigment epithelium. The administration of TGF-β can help promote healing of the atrophied retinal pigment epithelium in a controlled fashion, which is designed to limit excessive fibroproliferation that may occur without such treatment.

"Secondary cataracts" are opacities in the ocular lens which interfere with vision. Secondary cataracts occur after x-ray exposure, in diabetes, Wilson's disease and galactosemia, and as side effects in drug therapy. TGF-β can be used to promote healing of the lens after damage in a modulated fashion which is designed to limit hyperproliferation which can occur naturally.

The term "diseased corneal tissue" includes damage to the cornea by a variety of causes including, but not limited to, trauma, dry eyes (in which the conjunctiva on the inside of the eyelid may abrade the cornea), excessive light, allergens and infectious agents. TGF-β can be used to promote gradual healing of diseased corneal tissues and avoid excessive scarring which can interfere with vision.

"Sjögren's syndrome" is an autoimmune disorder which frequently is characterized by dry eyes, due to destruction of the tear glands by the autoimmune process. TGF-β can be used to control at least the ocular manifestations of Sjögren's syndrome. While not wishing to be bound by any particular theory, it appears that first TGF-β can promote gradual healing without scarring of the tear gland and that second, TGF-β also promotes healing of corneal epithelial wounds which arise from the dry eye syndrome caused by lack of tear glands. "Ocular neovascularization" is herein defined as the unwanted new growth of blood vessels into the ocular tissues. Unchecked, such growth can result in blindness. The ocular tissues which can be invaded by neovascularization include the cornea, iris, retina, vitreous, and choroid. Many diseases and conditions cause or contribute to ocular neovascularization. Causes of corneal neovascularization include but are not limited to trauma, chemical burns or corneal transplantation. Causes of neovascularization of the iris include but are not limited to diabetic retinopathy, vein occlusion, ocular tumor and retinal detachment. Causes of retinal and intravitreal neovascularization include but are not limited to diabetic retinopathy, vein occlusion, sickle cell retinopathy, retinopathy of prematurity, retinal detachment, ocular ischemia and trauma. Causes of choroidal neovascularization include but are not limited to retinal disorders of age-related macular degeneration, presumed ocular histoplasmosis syndrome, myopic degeneration, angioid streaks and ocular trauma.

"Treating a mammal for ocular neovascularization" is herein defined as treating ocular neovascularization which has already become detectable. "Mammals" are defined as humans and mammalian farm and sport animals and pets. Farm animals include, but are not limited to, cows, hogs, and sheep. Sport animals include, but are not limited to, dogs and horses. The category pets includes, but is not limited to, cats, dogs, and hamsters.

The method can involve the placement of at least an effective amount of a growth factor such as TGF-β, preferably TGF-β2, on the ophthalmic abnormality. Specifically, for treatment of macular holes, a concentrated solution of TGF-β or TGF-β2 is placed on the macular hole itself and/or the edges of the macular hole. Such treatments provide improvement of vision and healing by decreasing the thickness of the edge of the hole. The edges of the hole appear to adhere to choroid or reconnect with the posterior hyaloid membrane. Similarly, use of the growth factor on other retinal abnormalities is effective.

In one aspect of the invention, TGF-β2 is applied using known surgical techniques, such as those described in the example which follows. It is desirable that the TGF-β2 stay in place for a substantial period of time after application. For instance, a day is typically considered adequate for this purpose. To help retain TGF-β2 in place, known pharmaceutic combinations may be used. Hyaluronic acid is typically used in the eye for this purpose; however, as indicated by the data below, hyaluronic acid does not appear to increase treatment effectiveness.

A TGF-β dose of at least 1000 ng is preferred for at least partial alleviation of macular hole detachment. More preferred is a TGF-β dose of at least about 1100 ng. These doses appear to be the approximate dosage for improvement of vision (at least two lines on the Snellen Vision Chart). Although it is permissible to dissolve or suspend TGF-β2 in suitable ophthalmic carriers such as normal saline solution, we prefer to apply the material in a relatively concentrated form. The concentration may be measured by known light transmittance (210 or 280 nm wavelength) techniques and comparison with a standard curve. Preferably, the concentration is measured by light absorption at 280 nm.

This inventive treatment is applicable to retinal disorders, particularly to macular degeneration and holes, where it promotes healing and significantly improves vision. The treatment also may be used on peripheral retinal holes and tears.

The formulation, method of administration and dosage will depend upon the disorder to be treated, the point at which the disorder is being treated, and perhaps other aspects of the medical history of the patient. These factors are readily determinable in the course of therapy. Suitable patients with an ophthalmic disorder can be identified by medical history, physical findings and laboratory tests. The medical history reveals such facts as time of onset of symptoms such as red sclera, pain, photophobia, dry or gritty eyes, and vision changes, such as blurred vision not correctable with eyeglasses and double vision in an eye. Patients sometimes complain of inability to engage in their usual activities, such as watching television or driving a car at night.

Patients with ophthalmic disorders associated with impaired healing may have physical findings such as injected sclera, cotton-wool spots on the retina, a macular hole, bleeding behind the retina. Indicative laboratory results include low levels of TGF-β in the serum or in eye tissues, such as the vitreous.

TGF-β may be administered by any of a variety of routes known in the art, including but not limited to, intraocular, subretinal, subscleral, intrascleral, intrachoroidal, and subconjunctival injection, depending on the nature and location of the pathology being treated. Also contemplated in the present invention are administration by intravenous injection, subcutaneous injection, or oral administration, provided that sufficient TGF-β reaches the condition being treated. In one preferred embodiment, a concentrated solution of TGF-β is injected into the eye and placed immediately over the lesion, for example, on the retina.

TGF-β may be administered in any pharmaceutically acceptable formulation, including, but not limited to, solutions, suspensions, and timed-release preparations, such as microcapsular particles and implantable articles.

TGF-β generally exhibits poor stability in aqueous solution at neutral pH. TGF-β instability may be due to poor solubility at neutral pH or to adsorption to walls of vessels, tubing, syringes and the like. TGF-β is preferably stored at acidic pH in an alcoholic solution for increased stability. For administration to patients, the TGF-β solution should normally be adjusted to neutral pH, ie., pH 6–8. Preferably, the TGF-β solution is neutralized by dilution of the acidic concentrate with a buffered diluent. The diluent may contain excipients that are well known in the art, such as proteins, including human serum albumin, detergents and/or surfactants, salts, and the like. Dilution/neutralization of concentrated acidic TGF-β solutions may lead to some apparent protein loss due to aggregation of TGF-β molecules during the mixing process. Protein loss during mixing is easily and routinely determined by simply measuring the amount of TGF-β in the concentrated acidic solution, then measuring the amount of TGF-β, in the dilute, neutral solution. The amount of TGF-β may be measured by any of a number of methods well known in the art, such as immunoassay, e.g., ELISA, measuring light absorbance at 210 nm or 280 nm, or bioassay.

TGF-β is known to adsorb to the surfaces of many materials. Surface adsorption of TGF-β is increased when the TGF-β is in neutral pH solution. Preferably, neutral pH TGF-β solutions are mixed and stored in polyethylene or polypropylene containers and are dispensed/administered using instruments and/or devices made of or lined with polyethylene or polypropylene. Other materials, such as polystyrene and polyvinylchloride plastics and glass, can adsorb TGF-β from neutral solutions. For accurate determination of the dose delivered to a patient, it is preferred that the containers/instruments/devices involved in the mixing, storage and administration of TGF-β solutions be tested for adsorption. Adsorption of TGF-β from solution may be easily and routinely determined by simply measuring the amount of TGF-β in a solution before and after exposure to the container, instrument, or device in question. The amount of TGF-β may be measured by any of a number of methods well known in the art, such as immunoassay, e.g., ELISA, measuring light absorbance at 210 or 280 nm, or bioassay.

To achieve wound healing and improve visual acuity after treatment of retinal disorders, the preferred dose is greater than about 1000 ng (measured at an absorbance of 210 or 280 nm wavelength). Unless otherwise specified, all weights of TGF-β are based on measurements performed at 210 or 280 nm wavelength. More preferably, the dose is about 1100 ng. For some conditions, the preferred dose is about 2500 ng.

Alternatively, TGF-β2 may be administered in a slow-release device embedded in the tissue stroma or in a compartment adjacent to the affected tissue. For example, 1,000 ug of TGF-β in a pellet of ethylene vinyl copolymer 2 mm in diameter could be surgically implanted in the vitreous cavity or suprachoroidal space to release TGF-β over time. This modality is believed to be particularly beneficial for neovascularization of the iris or choroid.

Patients at risk for ophthalmic healing problems include those who have undergone or about to undergo surgery. Examples of such surgery include, but are not limited to, Cataract extraction, with or without lens replacement;

Corneal transplant for treating viral infections or penetrating keratoplasty (PKP);

Glaucoma filtration surgery; and

Radial keratotomy and other types of surgery to correct refraction.

In these conditions, the administration of TGF-β promotes prompt, gradual healing without excessive fibrous tissue formation.

Other growth factors which have both wound healing and neurotrophic effects can be applied in certain of these inventive treatments. These factors include, but are not limited to, acidic and basic fibroblast growth factor, insulin, insulin-like growth factor, platelet-derived growth factor, nerve growth factor, epidermal growth factor, transforming growth factor α, colony-stimulating factor, keratinocyte growth factor, and tissue plasminogen activator.

EXAMPLE 1

In this example, the effectiveness of TGF-β2 in alleviating macular holes is shown. Clinical data are provided in a table which follows this example.

Materials and Methods

Sixty eyes (60 patients) with Stage 2, 3, or 4 macular holes were treated. Thirty-two of the 60 patients had macular holes in both eyes. Patients ranged in age from 11–76 years, with a mean age of 63. All treated eyes had biomicroscopic evidence of a Stage 2, 3, or 4 macular hole confirmed by at least two independent observers. All but 5 eyes had the macular holes present for one year or less; all patients had subjective decreases in visual acuity as well as subjective distortions of vision. None of the patients had previous histories of cystoid macula edema, diabetic retinopathy, or exudative age-related macular degeneration.

Before treatment, technicians who were not told the planned treatment obtained best corrected Snellen visual acuity and performed intraocular pressure measurements, fundus photographs, and fluorescein angiography. Each macular hole was graded as Stage 2, 3, or 4 according to the criteria described by Gass (Arch. Ophthalmol. (1988) 106:629–39). Briefly, eyes with Stage 2 holes have a retinal dehiscence along the margin of the area of deep retinal cyst formation. In Stage 3, typically there is a full-thickness hole with overlying operculum. Macular holes are classified as Stage 4 when a posterior vitreous detachment is present. Treatment was scheduled within 2 weeks of the baseline examination. Under the criteria, patients were excluded if they had greater than 2+ nuclear sclerotic or posterior subcapsular lens changes. Patients were followed for 6–10 months, with mean follow-up of 8 months.

Treatment Groups

Doses of 45 ng, 220 ng, and 910 ng of TGF-β2 were administered. The 45 ng dose was chosen to provide a negative control for the higher doses. The 220 ng dose was believed to be at the low end of the effective range, and the 910 ng dose was believed to be well within the effective range. The dosages were calculated compensating for (a) adsorption of TGF-β to the PVC viscodissector (6% loss) and (b) protein loss during dilution/neutralization of the concentrated, acidic TGF-β solution (9% loss).

Eyes were randomly chosen for the indicated doses of intravitreal TGF-β2. In addition, some eyes separately received 100 μl of intravitreal hyaluronic acid at the time of instillation of TGF-β2 in an attempt to delay clearance of TGF-β2 from the area of the macular hole. Although effective in conjunction with TGF-β2, co-administration of hyaluronic acid appeared to lessen benefits from TGF-β2.

Surgical Procedure

All surgery was done under local anesthesia with sedation. After the eye was prepped and draped, a standard three-port vitrectomy was performed. In eyes with Stage 2 and Stage 3 macular holes, a core vitrectomy was performed. In many of these cases, a large central lacuna was found in the posterior one-third of the vitreous cavity, initially giving the impression that the posterior hyaloid was detached. However, in all of these eyes, further investigation revealed that the cortical vitreous remained on the retinal surface. In Stage 4 macular holes, a complete pars plana vitrectomy was performed at this point.

In some cases, an epiretinal membrane was found; however, no definite edges of this membrane could be found. Where encountered, the epiretinal membrane was peeled from the surface of the retina and removed from the eye. In other cases, no definite epiretinal membrane could be found; however, there appeared to be some gelatinous condensation on the inner surface of the retina surrounding the macular hole for approximately 200–400µ, with a firm adhesion along the margin of the macular hole. This was carefully dissected where possible; however, great care was exercised in order to limit traction on the edges of the macular hole or damage to the nerves.

After a short period of time to allow peripheral fluid to drain posteriorly, the fluid that had migrated posteriorly was aspirated. Typically, approximately 0.1–0.5 cc of fluid had reaccumulated on the retinal surface during this time. The center of the macular hole was gently aspirated to remove the last remaining amounts of fluid in the region of the macular hole.

A tapered, bent-tipped cannula was then connected to a 1 cc syringe containing a solution of TGF-$\beta$2. In each case, TGF-$\beta$2 was thawed and mixed within 2 hours of use. The TGF-$\beta$2 was supplied by Celtrix Pharmaceuticals, Inc., Santa Clara, Calif., and kept at $-70°$ C. until ready for use. It was always used within 2 hours of thawing and kept on ice until used. The TGF-$\beta$2 was highly purified (greater than 95% purity), and derived from bovine bone. The reconstituted formulation contained either 45, 220, or 910 ng/0.1 cc of TGF-$\beta$2 after dilution with a diluent solution. Eyes were randomly assigned a dose of TGF-$\beta$2. About 0.1 cc of TGF-$\beta$2 solution was gently infused into the macular hole. In about 50% of eyes, a comparable volume of hyaluronic acid was also introduced in order to determine if this might maintain the presence of the TGF-$\beta$2 solution, thereby improving efficacy.

After surgery, the patient was instructed to lie in a supine position for the first 24 hours following surgery; thereafter, the patient was instructed to remain in a face-down position as much as possible over the ensuing two weeks.

After surgery, patients were examined at 1 day, 2 weeks, 4–6 weeks, and monthly thereafter. Fluorescein angiography was performed at 4 to 6 weeks, 3 months, and 6 months. Best corrected Snellen visual acuity, intraocular pressure, lens status, bubble size, status of macular hole, and occurrence of adverse effects were determined at each examination.

Statistical Analysis

Treatment effects were assessed using logistic regression. The dependent variable was improvement in visual acuity of two or more lines on the Snellen Chart, and the independent variables were TGF-$\beta$2 dose and hyaluronic acid use.

Results

At the time of surgery the status of the posterior hyaloid surface as well as the stage of the macular hole could be readily confirmed. As is shown in the table, of the 60 treated eyes, four had Stage 2 macular holes, 34 had Stage 3 macular holes, and 22 eyes had Stage 4 macular holes associated with posterior vitreous detachment.

Using the techniques described above, the posterior hyaloid surface was completely separated from the retina in all eyes with Stage 2 and Stage 3 macular holes. However, in all eyes with Stage 2 macular holes, this separation of the posterior hyaloid surface from the retina extended marginal dehiscence and formed an operculum that was elevated from the posterior hyaloid surface. In one eye, the retina was torn in the inferotemporal quadrant between the ora and the equator and accompanied by an adjacent intraretinal hemorrhage. This retinal tear was treated without consequence with transscleral cryopexy.

After vitrectomy, all eyes had a 200–400 µ band of gelatinous material on the inner retinal surface along the margin of the macular hole. Small amounts of this material could be dissected from the retina, but it could not be removed in a continuous sheet, as is typical for idiopathic fibrocellular epiretinal membranes. Aggressive dissection was avoided to minimize trauma to the macula.

On the first and second post-operative days, the anterior chamber had only trace amounts of flare and cell in all eyes except six. In these six eyes, a fine, red-brown precipitate was found on the endothelial surface of the cornea along with minimal striae. In all cases, the precipitate and striae resolved within two weeks without sequelae. All eyes with intact lenses had mild to moderate posterior lens feathering which resolved within two weeks.

. All eyes had bubbles filling at least 75% of the vitreous cavity on the first and second post-operative day. The intraocular pressure was not higher than 30 mm Hg. None of the eyes had a significant inflammatory response two weeks post-operatively. All eyes had a bubble filling at least 60% of the vitreous at that time. After four to six weeks, the bubble filled 30% to 40% of the vitreous cavity.

At four to six weeks, the macular region could be adequately examined using a biomicroscope with a contact lens or a 78 diopter lens. Microscopic retinal detachment and retinal thickening surrounding the macular hole could be readily assessed at this time. As is shown in the table, flattening of the detachment and thinning of the adjacent retina to a normal-appearing thickness occurred in 12/12 eyes treated with 220 ng of TGF-$\beta$2 without hyaluronic acid and 11/11 eyes treated with 910 ng of TGF-$\beta$2 without hyaluronic acid. In contrast, only 6/11 eyes treated with 45 ng TGF-$\beta$2 without hyaluronic acid had the edges of the macular hole flatten after 4–6 weeks. The addition of hyaluronic acid to the TGF-$\beta$2 gave unexpected results. As the data in the table indicate, hyaluronic acid significantly suppressed the rate of flattening of the retina around the macular hole.

Visual acuity did not improve in eyes with no improvement in retinal flattening. Final visual acuity improved two lines or more in 10/11 eyes treated with 910 ng TGF-$\beta$2 without hyaluronic acid, 4/12 eyes treated with 220 ng TGF-$\beta$2 without hyaluronic acid, and 5/11 eyes treated with 45 ng TGF-$\beta$2 without hyaluronic acid.

In contrast, the addition of hyaluronic acid appeared to suppress visual improvement. Final visual acuity improved two lines or more in 4/9 eyes treated with 910 ng TGF-$\beta$2 and hyaluronic acid, 2/8 eyes treated with 220 ng TGF-$\beta$2 and hyaluronic acid, and 0/9 eyes treated with 45 ng TGF-$\beta$2 and hyaluronic acid.

Logistic regression analysis was performed using two-line improvement in visual acuity as the outcome variable and use of TGF-$\beta$2 and hyaluronic acid as independent variables. The analysis demonstrated a statistically significant beneficial effect of TGF-$\beta$2 on visual improvement ($p=0.003$). In contrast, the analysis demonstrated that the use of hyaluronic acid reduced the chance for visual improvement ($p=0.002$).

Most eyes developed a subtle, localized layer of fibrous tissue along the edge of the macular hole. This fibrous tissue could sometimes be seen to span the macular hole. In spite of this fibrous tissue formation, no eyes developed a traction retinal detachment or significant macular traction.

Additionally, angiographic findings improved. Preoperatively, fluorescein angiography revealed a central hyperfluorescent window defect corresponding to the base of the macular hole in most eyes. Postoperatively, angiography showed a decrease of the central hyperfluorescence in most eyes in which the edges of the macular hole had flattened. However, the hyperfluorescence persisted in all eyes with persistent subretinal fluid and retinal thickening surrounding the macular hole.

Discussion

We consider the control of wound healing to be important in the treatment of numerous retinal disorders. This example describes the first use of TGF-β in the treatment of a retinal disorder with improvement of vision.

The rationale for treatment in this example was to induce flattening of the edges of the macular hole in order to resolve retinal detachment and thickening surrounding the hole. Knowledge of the behavior of peripheral retinal holes suggests that reducing the traction force which elevates the retina around the hole coupled with the inducing chorioretinal adhesion along the edge of the hole may be required. Unlike peripheral retinal holes where surgical techniques can be used to reattach the retina and a small area of destruction is not noticeable, macular holes require gentle induction of chorioretinal adhesion to avoid the destruction of adjacent neurosensory tissue and permanent destruction of central vision.

Visual improvement was achievable when significant degeneration of the neurosensory retina had not occurred secondary to the localized foveal detachment, and significant destruction of tissue does not result from surgical intervention. Again, experience with peripheral retinal holes and tears suggests that not all retinal traction need be removed, provided that the method induces a chorioretinal adhesion of sufficient strength to counteract the existing traction.

In this technique, the posterior hyaloid was separated from the retina in eyes having Stage 2 or Stage 3 macular holes. Next, a gelatinous, friable material accumulated along the margins of the holes, but only limited attempts were made to remove the material for fear of damaging the adjacent neurosensory tissue.

To avoid significant tissue damage but relieve traction along the margin of the hole, this method limits manipulation of the retina and induces chorioretinal adhesion using TGF-β.

As is shown in the Table, the edges of the macular holes were flattened in 23/23 (100%) eyes treated with 220 or 910 ng TGF-β2 without hyaluronic acid. In many of these eyes, a fine bead of fibrous tissue could be observed along the margin of the macular hole after it flattened. This fibrous tissue was accompanied with good visual recovery (vision improvement of two or more Snellen lines).

In this example, with limited manipulation of the macular hole, there was no enlargement of the macular hole or evidence of mottling of the retinal pigment epithelium surrounding the macular hole.

In this example, the fluorescein angiographically demonstrable hyperfluorescence over the base of the macular hole disappeared after the edges of the hole had flattened. The reduced fluorescence could be due to formation of an overlying fibrous membrane. However, judging by the thin, relatively clear appearance of the membrane, we believe this is not the cause. More likely is a redistribution of pigment within the retinal pigment epithelium (RPE) cells. Regardless of the explanation, the higher level of treatment improved the visual acuity of the treated eyes.

A major concern in this study was that TGF-β2 might cause excessive fibrosis which can increase macular contraction and result in proliferative vitreoretinopathy (PVR). TGF-β2 is known to be present in significant concentration in eyes with PVR, and has been implicated in its formation (See, Connor, *J. Clin. Invest.* (1989) 83:1661–66). However, the concentration of TGF-β2 used in these cases was significantly less than that seen in eyes with PVR. Notably, neither of these potential complications was seen in any of the 60 eyes treated; and all eyes were observed for at least six months after treatment.

Visual acuity improved in eyes with flattened edges of the macular hole, resorption of subretinal fluid, and thinning of the adjacent retina in response to TGF-β2.

As shown in the table, although the edges of the macular holes flattened successfully in all eyes in both the 220 ng and the 910 ng non-hyaluronic acid groups, visual improvement surprisingly occurred more commonly in eyes receiving the higher dose. More fibrous tissue formation is unlikely to account for this finding. While not wishing to be bound by a theory, we may postulate that TGF-β2 also enhanced recovery of the photoreceptor outer segment function, possibly by neural regeneration or stimulation of accessory tissues which in turn help stabilize and align neural retinal cells.

In a follow-up study, to ascertain the best dose, there were 30 eyes treated with placebo, 29 treated with 445 ng of TGF-β2 and 29 eyes treated with 1100 ng of TGF-β2. The 1 100 ng dose was surprisingly more effective than the 445 ng dose, particularly in improving visual acuity by three or more lines ETDRS by 12 months post-operatively. 30% of placebo eyes had such an improvement, 62% of 445 ng-treated eyes had such an improvement (p=0.019, not significantly different from placebo), but 75.9% of 1100 ng-treated eyes had such an improvement (p<0.001, highly significant). As for two-line improvement at 12 months, 69.0% of 445 ng-treated eyes improved (p=0.004) but 79% of 1100 ng-treated eyes improved (p<0.001). Mean line changes were calculated for each group and TGF-β2 groups were compared with placebo. At 12 months, placebo eyes improved 0.6 lines, 445 ng-treated eye improved 2.5 lines (p=0.037), and 1100 ng-treated eyes improved 3.8 lines (p<0.001). Thus, even compared to a dose of about 500 ng, there was marked improvement with the 1100 ng dose.

EXAMPLE 2

In this example, a process for the treatment of subretinal pigment epithelial (sub-RPE) or subretinal neovascularization using TGF-β2 is described.

Methods

The study involves 50 patients who satisfy the study criteria for sub-RPE or sub-retinal neovascularization. Patients are chosen according to the following criteria:

1. Biomicroscopic and fluorescein angiographic evidence of sub-RPE or sub-retinal neovascularization involving the foveal avascular zone;
2. Subjective visual decrease; and
3. Objective visual loss confirmed by visual acuity measurements.

However, patients meeting the following criteria are excluded from the study:

1. Patients who have been previously treated with TGF-β2 in the operative eye;
2. Patients currently pregnant or nursing;
3. Presence of any clinically significant condition (e.g., active proliferative diabetic retinopathy) which may be incompatible with participation in this study; and
4. Patients taking medications which would interfere with the evaluation of this study.

One group of patients is randomly assigned to receive a single intraoperative local dose of either 50 µl or 200 µl of 1.1 µg/ 100 µl of TGF-β2 applied directly to the foveal region. Another group of patients will be injected with 50 µl in the subretinal space and 150 µl within the vitreous cavity above the area of the sub-RPE or sub-retinal neovascularization. After twenty patients are treated, the data are evaluated to determine whether any safety modifications to the protocol are appropriate. If there are unusual side effects in the twenty treated eyes, such as proliferative vitreoretinopathy (PVR), excessive hemorrhage, or unexplained retinal detachment, the trial is stopped at this point.

Baseline studies include visual acuity measurement (standardized Snellen and ETDRS eye charts) and biomicroscopy, as well as both fluorescein and ICG angiography to document the presence of the sub-RPE or subretinal neovascularization. After treatment, patients are followed for one year. Safety and efficacy assessments include visual acuity measurements, biomicroscopic visualization of the fovea, and fluorescein and ICG angiography.

Surgical Procedures

All surgery is performed under either local anesthesia with sedation or general anesthesia. Two conjunctival flaps are made laterally and medially. Two additional sclerotomies are made at 10 o'clock and 2 o'clock meridians, 4 mm posterior to the limbus. A light pipe and vitreous cutter are then introduced. At this point, a core vitrectomy is performed in the involved eye. After the core vitrectomy, the vitreous cutter is removed and replaced with a cannula having a flexible silicone tip. Then the cannula is connected to an aspiration system. The tip of the cannula is inserted and positioned approximately 1 mm above the retinal surface but below the superotemporal arcade. After the posterior hyaloid surface is elevated in the area just inferior to the superotemporal arcade, the posterior hyaloid is detached as far as possible out to the equator. In some cases, additional manipulation is needed at the disc in order to complete the detachment of the posterior hyaloid surface. Once this is accomplished, a total pars plana vitrectomy is performed by removing the vitreous as far out to the periphery as possible. The retina is examined to assure that no retinal tears have occurred.

Freshly thawed TGF-β2 is suspended in buffer containing 2% human serum albumin for a concentration of 1.1 µg/100 µl TGF-β2 solution. TGF-β2 solution (either 50 µl or 200 µl) is applied to the area of neovascularization. In patients receiving subretinal TGF-β2, a bent, tapered 33-gauge cannula is used to enter the subretinal space at a site at least one disc diameter from the center of the fovea. Gentle injection of 50 µl containing 1.1 µg/ 100 µl TGF-β2 is performed. The additional 150 µl of TGF-β2 is injected within the vitreous cavity just over the area of neovascularization. The conjunctival flaps and sclerotomies are closed. The intraocular pressure is checked and the intravitreal bubble adjusted to achieve normal pressure. The patient receives acetazolamide, 500 mg IV, and is continued on acetazolamide, 250 mg PO or IV every six hours, for the next 24 hours. The patient is instructed to lie in a supine position for the first 24 hours following surgery; thereafter, the patient is instructed to remain in a face-down position as much as possible over the next five days.

Patients are examined at one day, two weeks, four to six weeks, and at three, six and twelve months after surgery. The patients are examined for best corrected visual acuity for both distance and near vision, refraction, intraocular pressure, size of neovascular net, presence of epiretinal membrane, presence of hyperfluorescence on fluorescein angiography, lens status, and results of ICG angiography.

Analysis and Results

Data resulting from this trial are analyzed to establish the safety and efficacy of these doses of TGF-β2. A treatment is considered successful if, corrected visual acuity improves (about two lines) or stabilizes in patients whose vision is 20/200 or better; or corrected visual acuity improves to 20/200 in patients whose vision is worse than 20/200, or there is a decrease in the size of the neovascular net.

Other Disorders

The inventive treatment is also considered to be beneficial in other ocular disorders such as retinal edema, retinal vascular disorders, wound healing disorders, proliferative ocular disorders, anti-degenerative disorders, anti-angiogenesis disorders, dry eye syndromes, uveitis, and various retinal detachments.

EXAMPLE 3

To investigate the effects of TGF-β1 and TGF-β2 alone on neovascularization in vivo, various doses of TGF-β were implanted into the clear cornea of rabbits, and the neovascular response was measured over time.

Five to seven pound male and female New Zealand White rabbits were used. The animals were anesthetized with subcutaneous injections of 20 mg of xylazine and 80 mg of ketamine every other day for a total of 4 anesthesias. While under anesthesia on day 6, the animals were euthanized with an intracardiac injection of 325 mg of sodium pentobarbital.

TGF-β1 and TGF-β2 and vehicle controls were placed in 2.5 isogel agarose (FMC Corp., Rockland, Me.). Porcine platelet-derived TGF-β1 and TGF-β2 lyophilized without bovine serum albumin (BSA) were obtained from Drs. Anita Robert and Michael Sporn (NIH, Bethesda, Md.). Porcine platelet-derived TGF-β1 lyophilized with BSA also was obtained from R&D systems, Inc. (Minneapolis, Minn.). The duplication of sources was used to help control for the method of procurement, handling and shipment variables. Prior to adding to the agarose, TGF-β1 and TGF-β2 were solubilized in 4 mM HCl. The agarose was heated to 60° C., added to the solubilized peptides and then allowed to gel at room temperature. The gelled agarose was then divided into 2×1.5×1 mm implants for implantation into the rabbit cornea.

Agarose implants containing 1,5,25 and 100 ng of TGF-β were placed within pockets in 7,6,6 and 4 corneas, respectively, on day 0. Corneas were photographed on days 2, 4 and 6. The photographs were developed as slides, which in turn were projected and the blood vessel lengths were measured.

When TGF-β1 was implanted into a nonvascular rabbit cornea, there was a dose-dependent stimulation of blood vessel growth in 82% of corneas implanted with 1,5,25 and 100 ng. The majority of corneas implanted with I ng of TGF-β showed no neovascular ingrowth. The remaining 1 -ng-treated corneas had sparse, short blood vessels. As the dose increase from 5 to 100 ng, the neovascularization became more dense, the blood vessels were longer, and the corneas became more edematous. At two days post-implantation, an intrastromal neovascular response was evident and became more prominent at days 4 and 6.

However, in corneas implanted with 100 ng of TGF-β, blood vessel formation appeared to be impeded adjacent to the TGF-β-containing implant. This effect was not observed when neovascularization was stimulated by TGF-alpha or PGE 1 (see below), suggesting that the implant did not merely act as a mechanical barrier impeding the growth of new blood vessels.

Thus, administering TGF-β1 I or TGF-β2 without any preexisting neovascularization may cause neovascularization to develop.

EXAMPLE 4

The triple pocket corneal assay includes first administration of an agent to produce neovascularization in one compartment, followed by implantation of TGF-β1, TGF-β2 or a control on both sides of the neovascularization.

First, neovascularization was induced by implanting a pellet containing either PGE1 (Upjohn Co., Kalamazoo, Mich.) or TGF-alpha (Chemicon International, Inc., El Segundo, Calif.). The PGE 1 was solubilized in absolute alcohol and then added to a casting solution of 10% ethylene vinyl coacetate polymer in methylene chloride to form pellets. TGF- α was solubilized in 1 mM HCl and then added to agarose and divided into implants. Two days later (day 0 of the TGF-β study), TGF-β1, TGF-β2 or control pellets were implanted next to actively growing blood vessels and on either side of the primary implant to test for the effect on the angiogenic activity. TGF-β1 and TGF-β2 were used at doses of 1,3,5,10,25,100 and 200 ng (6 corneas for each dose, except for 8 for the 100 ng dose). In addition, TGF-β1 was implanted at the 50 ng dose. Control agarose implants contained an equivalent volume of vehicle (4 mM HCl) or 100 ng of platelet-derived growth factor (PDGF from R&D Systems, Inc.) solubilized in 4 mM HCl.

The pockets for the secondary implants were formed by one-half-thickness incisions which were 1.5 mm long and perpendicular to and 1.5 mm from the limbus and 3–4 mm from the primary implant. Two pockets were formed on either side of the primary implant by gently inserting a cyclodialysis spatula into the incised edge of the cornea and advancing the spatula in a plane parallel to the curvature of the cornea to within 1.0 mm of the primary implant such that the pockets lay 1.5 mm from and parallel to the limbus.

Blood vessel lengths were measured adjacent to the TGF-β -containing implant (E) and the control implant (C) 2 mm from the center of the primary implant (FIG. 1). The relative lengths of the blood vessels in these areas were then expressed as a ratio: E/C (the length of the blood vessels in the area of the TGF-β implant divided by the length of the blood vessels in the area of the control implant). Percent stimulation or inhibition was calculated by subtracting 1.0 from E/C and multiplying by 100. Measurements of blood vessel length adjacent to both the TGF-β and control implants were made from projected slides taken at days 2,4 and 6.

Serial 5-micron frozen sections were taken from a cornea implanted with 100 ng of TGF-β in a triple pocket assay, stained with hematoxylin and examined by light microscopy.

TGF-β enhanced neovascularization in 89% of corneas at doses of 1,3 and 5 ng. At 1 ng, neovascularization was enhanced by 47%; at 3 ng, 118%; and at 5 ng, 67% relative to control on day 4. TGF-β1 stimulated neovascularization much more than TGF-β2 at the 1 ng dose (about 55% and 40%, respectively) and 3 ng dose (180% and 56%, respectively).

In contrast, in 100% of corneas receiving 25–100 ng of TGF-β1 and TGF-β2 neovascularization was inhibited relative to control as shown in the following table. TGF-β1 and TGF-β2 were comparable in effectiveness.

| INHIBITION OF NEOVASCULARIZATION BY DOSE AND LENGTH OF IMPLANTATION TIME | | | |
|---|---|---|---|
| Dose | Day 2 | Day 4 | Day 6 |
| 25 ng | 52% | 42% | 33% |
| 100 ng | 68% | 53% | 56% |
| 200 ng | 66% | 56% | 46% |

In addition, the 50 ng dose of TGF-β1 inhibited neovascularization by 59% on day 2,49% on day 4 and 29% on day 6. The dose of 10 ng appeared to be a transitional dose at which two of six corneas showed stimulation of neovascularization in the area of the TGF-β implant and four of six had neovascularization relative to the control.

Thus, both TGF-β1 and TGF-β2 can inhibit neovascularization caused by PGE1 or TGF-α. The inhibition was found to be dose dependent, with doses greater than 10 ng inhibiting neovascularization. The optimal dose in this experiment appeared to be about 100 ng. Overall, TGF-β2 is superior in having less stimulatory effect and greater safety while offering equivalent neovascularization inhibition.

While not wishing to be bound by any particular theory, the inventors propose that the different effects above and below 10 ng may be due to the interplay of TGF-β on multiple functions, including causing chemotaxis in blood monocytes at about 0.1 to 1.0 pg/ml, inducing gene expression for interleukin-1 (at least IL- 1β-specific mRNA has been observed in cultured monocytes) at 1.0 to 25 ng/ml, and inhibiting vascular endothelial cell proliferation at 0.1 to 10.0 ng/ml. Thus, at less than 10 ng, the effect on vascular endothelial cell proliferation appears to predominate; whereas, at higher doses, effects on cellular function which could inhibit neovascularization.

EXAMPLE 5

In this experiment, 1 00 ng of PDGF and 100 ng of TGF-β1 and TGF-β2 (four corneas for each peptide) were the secondary implants after the initial 1.5 ug PGE1 neovascular stimulus. TGF-β inhibited neovascularization relative to PDGF in 100% of corneas. TGF-β1 and TGF-β2 showed comparable degrees of inhibition. The average blood vessel length in the area of the TGF-β implant was 19%, 40% and 36% of the average blood vessel length in the area of the PDGF implant on days 2, 4 and 6, respectively (combined data for β1 and β2).

In this experiment, 100 ng of PDGF and 100 ng of TGF-β1 and TGF-β2 (six corneas for each peptide) were the secondary implants after the initial 300 ng TGF-α neovascular stimulus. TGF-β also inhibited neovascularization stimulated by TGF-α at a dose of 300 ng. TGF-β inhibited neovascularization in 100% of corneas. TGF-β1 and TGF-β2 had comparable degrees of inhibition. The combined average blood vessel length in the area of the TGF-β implant was 47%, 51% and 47% of the blood vessel lengths around the control implant on days 2, 4 and 6, respectively.

In addition, 5 micron frozen sections were taken from a cornea implanted with 100 ng of TGF-β in a triple pocket assay, hematoxylin stained and examined by light microscopy. An increase in cell number was observed in the stroma surrounding the TGF-β implant when compared to the control implant. No evidence of tissue edema or tissue necrosis was observed in these section. No strong inflammatory cell infiltrate was observed around either of the pellets.

In these experiments, TGF-β1 and TGF-β2 were compared with PDGF, which served as a negative protein control. Thus, this experiment indicates that the anti-neovascularization effects of TGF-β1 and TGF-β2 are specific to these proteins and are not due to administering protein.

EXAMPLE 6

In this experiment, the effect of TGF-β2 on healing after corneal surgery for correction of myopia and hyperopia is determined by measuring the magnitude of effect that TGF-β2 has on altering the corneal topography in three different types of corneal incisions.

Female cats weighing 7–9 pounds are used because the eye is similar in size, shape and morphology to that of humans. Similarly, their corneal endothelial cells have limited mitotic capability. It has also been demonstrated that cat corneas heal very much like human corneas. Thus, the cat is an excellent model to study corneal wound healing.

Radial non-penetrating radial incisions are made. One group of animals receives two radial incisions and the other group receives four radial incisions using a knife with micrometer adjusted to cut up to 90% of the central corneal thickness. Both eyes are operated. With the aid of an operating microscope, the 3.5 mm central optical zone centered over the pupil is demarcated with a marker. Radial incisions start at the central optical zone and extend peripherally to within about 2–3 mm of the limbus. Circular incisions are made with corneal trephines of different diameters and penetrate about 90% of the corneal depth. At the end of surgery, 2.0 μg or 5.0 μg TGF-β2 or control solution is applied to each eye. In some eyes with nasal and temporal incision, TGF-β2 is applied to one incision (after which a cup is placed over the incision to keep the medication from dispersing) and the other incision is not treated. This helps assess the effect of TGF-β2 on the change in topography. Next, antibiotic ointment is topically applied to the eyes.

The eyes are observed under the slit lamp and corneal topographic measurements are made, both before and at regular intervals after surgery. The slit lamp is used to evaluate corneal vascularization, epithelial healing, depth of incisions (to assess healing) and the amount of scar tissue formed. Corneal topographic measurements will help assess how symmetrically and quickly the eyes stabilize. At the end of the study, the cats are euthanized, and sections of the eyes are mounted on slide, stained and compared. The eyes receiving TGF-β2 treatment have rapid, strong healing and early stabilization of corneal topography.

EXAMPLE 7

In this example, bovine bone-derived TGF-β2 (bTGF-β2) was applied onto the macula of patients with CME following vitrectomy with the intent to reduce the magnitude of retinal edema and to improve visual acuity. Ten patients with persistent CME, and meeting the other entry requirements of the study, receive a vitrectomy plus bTGF-β2 applied directly onto the macular lesion at its interface with the vitreous cavity. Study participants are examined at baseline and selected intervals post-treatment. Parameters to be assessed include visual acuity (EDTRS eye chart), macular status (biomicroscopy and fluorescein angiography), adverse events (lens status, intraocular pressure, and retinal detachment), and concomitant medications.

Patients are chosen according to the following criteria:

1. Biomicroscopic and fluorescein angiographic evidence of cystoid macular edema (CME)
2. CME present for at least 3 months but not more than 12 months
3. Patient failed to respond to treatment with one or more anti-inflammatory agents
4. Previous cataract extraction with or without lens implant
5. Best corrected visual acuity between 20/60 and 20/800
6. Patient can comply with all aspects of the treatment and evaluation schedule
7. Patient can provide voluntary informed consent However, patients having any of the following are excluded from the study:

1. Prior posterior vitrectomy with or without TGF-β2 treatment
2. Other ocular disease (e.g. macular degeneration, diabetic retinopathy, macular hole, retinal detachment, advanced glaucoma, etc.) which could interfere with macular function
3. Significant ocular media opacity which interferes with determining best corrected visual acuity
4. Uveitis unrelated to cataract surgery
5. Nursing or pregnant patient
6. Potentially unable to complete entire follow-up schedule Patients who appear to meet the subject eligibility criteria undergo baseline evaluation. Baseline findings that are not consistent with the requirements of the study cause discontinuation of the patient from the study. Baseline studies include a complete medical and ophthalmologic history and an ophthalmic examination with visual acuity measurements. Best corrected visual acuity is measured using the ETDRS eye chart. CME is confirmed by slit lamp biomicroscopy using a fundus contact lens or 78 diopter lens. Color fundus photographs (30°) are taken of the disc and macula (photographic fields I and II). Fluorescein angiography is used to confirm the diagnosis of CME using stereoscopic angiography. Stereo red-free photographs are also taken of the macula at the beginning of the angiogram. The transit frames of the angiogram are centered on the macular (field II) of the study eye, with frames taken at 30 seconds, 1 minute, 2 minutes, 5 minutes, and 10 minutes. A stereo photograph of the disc (field I) is also taken at 10 minutes. All study photographs are labeled with the patient's study code and the date of the photograph, and subsequently graded by a certified grader who is masked with regard to either the patient's study code or the time the photographs were taken relative to treatment.

Treatment is scheduled within one week (seven days) of the date on which the baseline tests are completed. If for any reason treatment is postponed, all baseline studies must be repeated.

All surgery is performed under local anesthesia with standby anesthesia, unless the investigator or patient wants the procedure to be performed under general anesthesia. After the eye is prepped and draped, a lid speculum is positioned. Two conjunctival incisions are made in the temporal and nasal conjunctiva, and a 4 mm infusion cannula is sutured 3 mm posterior to the limbus in the inferotemporal quadrant using a preplaced 4–0 white silk suture. Before the vitreous infusion solution is started, it is established that the infusion cannula tip is indeed in the vitreous cavity. Two additional sclerotomies are made in the superotemporal and superonasal quadrants, 3 mm posterior to the limbus. A vitreous cutter and fiberoptic light pipe are then introduced into the vitreous cavity. The anterior and central vitreous are removed. Any visible vitreous adhesions to the anterior segment, iris, or lens capsule are severed. The posterior vitreous is then removed with the vitreous cutter. Each eye is examined for a posterior vitreous detachment using a flexible silicone tip cannula attached to the suction line of the vitreous cutter console. A suction of 150 mm Hg is applied approximately 2–3 mm superior to the fovea, about 0.2 to 0.5 mm anterior to the retina, to determine if there is residual posterior cortical vitreous with an attached posterior hyaloid. If the posterior hyaloid is still attached, the silicone tip cannula is used to create a posterior vitreous detachment. The posterior hyaloid is removed with the vitreous cutter to at least the equator. The silicone tip cannula is used to verify that the posterior hyaloid has been completely removed posterior to the equator.

The vitreous cutter and fiberoptic light pipe is removed from the eye, and the sclerotomies closed with scleral plugs. The peripheral retina is examined with indirect ophthalmoscopy and scleral depression to look for any peripheral retinal breaks. Peripheral breaks, if present, are treated with cryopexy. The scleral plugs are then removed, and the light pipe and silicone tip cannula are reintroduced into the vitreous cavity. A fluid-air exchange is performed, aspirating the intravitreal fluid over the optic nerve. The instruments are removed, and the scleral plugs replaced. Fifteen minutes is allowed for accumulation of fluid from the peripheral retina and vitreous base around the optic nerve. The scleral plugs are again removed, and the remaining fluid anterior to the optic nerve aspirated using the silicone tipped cannula.

The viscodissection cannula and tubing (Visitec) are then connected to a 1 cc syringe containing TGF-β2 freshly diluted in neutral buffer supplemented with 2% human serum albumin. The tip of the viscodissection cannula is positioned directly over the fovea, taking care not to touch the fovea with the cannula. A 0.1 ml aliquot (1.1 µg) of TGF-β2 is injected over the macula. The instruments are removed from the eye, and the two superior sclerotomies closed with 7–0 vicryl suture. The infusion cannula is removed, and the remaining slerotomy closed with 7–0 vicryl suture. The intraocular pressure is normalized with sterile air to achieve an intraocular pressure of about 10 mm Hg. The conjunctiva is then closed with interrupted 6–0 collagen suture. The patient is instructed to lie in a supine position for the first 24 hours following surgery; thereafter, the patient is instructed to remain in a facedown position as much as possible over the ensuing five days.

On Day 1 and Week 1, the following parameters are assessed: Intraocular pressure (if abnormally high, IOP is treated first with topical aqueous suppressants such as β-blockers or α-blockers; oral carbonic anhydrase inhibitors are only used if topical therapy has been deemed inadequate to control the intraocular pressure); the size of the gas bubble remaining; the anterior segment, including the cornea, anterior chamber, and lens, with slit lamp biomicroscopy; adverse events; and concomitant medication.

At weeks 2 and 6, and months 3, 6, and 12 post-treatment, the following parameters are assessed: best corrected vision using standard refraction and the ETDRS chart; intraocular pressure; lens status including the magnitude of nuclear sclerosis and posterior subcapsular cataract formation, both of which are graded on a scale of 0–4; the severity of cystoid macular edema is assessed by slit lamp biomicroscopy on a 04 scale; the severity of cystoid macular edema from fluorescein angiographic photographs by a certified grader who is masked with regard to patient identity and visitation date; the presence or absence of an epiretinal membrane; adverse events; and changes in concomitant medications.

The invention has been described by example and by words. It is the Inventors' intent that the examples not be used to limit the scope of the invention and further that equivalents to the claims expressed below be considered within the scope of the invention.

TABLE

| Dosage | Patient No. | Age | Stage | Flattening of Edge (Y/N) | Pre-Op | Final | (Y/N) |
|---|---|---|---|---|---|---|---|
| (45 ng) | 30 | 74 | 4 | Y | 20/400 | 20/100−1 | Y |
| (Without | 33 | 67 | 2 | N | 20/200 | 20/400 | N |
| Hyaluro- | 35 | 61 | 4 | N | 20/60−1 | 20/400 | N |
| nic Acid) | 38 | 69 | 3 | N | 20/400 | 20/400 | N |
| | 41 | 62 | 3 | Y | 20/200−1 | 20/50−2 | Y |
| | 45 | 74 | 3 | Y | 20/200+1 | 20/60+1 | Y |
| | 48 | 63 | 3 | N | 20/80 | 20/400 | N |
| | 49 | 72 | 3 | N | 20/200 | 20/400 | N |
| | 54 | 72 | 4 | Y | 20/400 | 20/200+1 | N |
| | 56 | 66 | 4 | Y | 20/200 | 20/80−1 | Y |
| | 58 | 72 | 4 | Y | 20/200 | 20/50+2 | Y |
| Total Flattened: 6/11 | | | | | | Total Improved: 5/11 | |
| (220 ng) | 1 | 72 | 4 | Y | 20/200 | 2/60 | Y |
| (Without | 28 | 60 | 4 | Y | 20/200+1 | 20/50 | Y |
| Hyaluro- | 32 | 66 | 2 | Y | 20/100−2 | 20/100 | N |
| nic Acid) | 36 | 63 | 3 | Y | 20/200+1 | 20/70−1 | Y |
| | 39 | 62 | 4 | Y | 20/200 | 20/400 | N |
| | 42 | 68 | 3 | Y | 20/70+1 | 20/200 | N |
| | 44 | 11 | 3 | Y | 20/200 | 20/200 | N |
| | 47 | 66 | 3 | Y | 20/200 | 20/200 | N |
| | 50 | 61 | 3 | Y | 20/80−1 | 20/200 | N |
| | 52 | 66 | 3 | Y | 20/60−1 | 20/200 | N |
| | 55 | 53 | 3 | Y | 20/70+1 | 20/50+1 | Y |
| | 59 | 55 | 4 | Y | 20/80−2 | 20/80+1 | N |
| Total Flattened: 12/12 | | | | | | Total Improved: 4/12 | |
| (910 ng) | 29 | 61 | 3 | Y | 20/200 | 20/70−1 | Y |
| (Without | 31 | 66 | 3 | Y | 20/100−2 | 20/40 | Y |
| Hyaluro- | 34 | 72 | 3 | Y | 20/200 | 20/60+1 | Y |
| nic Acid) | 37 | 67 | 4 | Y | 10/50−2 | 20/50−2 | N |
| | 40 | 69 | 4 | Y | 20/80−1 | 20/60 | Y |
| | 43 | 69 | 4 | Y | 7/200 | 20/200−1 | Y |
| | 46 | 65 | 3 | Y | 20/100−2 | 20/40−2 | Y |
| | 51 | 73 | 3 | Y | 20/100−2 | 20/50−2 | Y |
| | 53 | 70 | 4 | Y | 20/100−2 | 20/70 | Y |
| | 57 | 58 | 3 | Y | 20/200 | 20/80−1 | Y |
| | 60 | 69 | 4 | Y | 20/80−1 | 20/40 | Y |
| Total Flattened: 11/11 | | | | | | Total Improved: 10/11 | |
| (45 ng) | 2 | 60 | 4 | N | 20/200+1 | 20/400 | N |
| (With | 6 | 70 | 3 | N | 20/200 | 20/400 | N |
| Hyaluro- | 9 | 72 | 3 | Y | 20/200 | 20/400 | N |
| nic Acid) | 12 | 64 | 3 | N | 20/400 | 20/400 | N |
| | 13 | 66 | 3 | N | 20/80+2 | 20/400 | N |
| | 16 | 65 | 4 | N | 20/200 | 20/200−1 | N |
| | 18 | 68 | 2 | N | 20/100−2 | 20/400 | N |
| | 23 | 69 | 3 | N | 20/100 | 20/200 | N |
| | 26 | 49 | 3 | N | 20/80−2 | 20/100 | N |
| Total Flattened: 1/9 | | | | | | Total Improved: 0/9 | |
| (220 ng) | 5 | 66 | 3 | Y | 20/80−1 | 20/50−2 | Y |
| (With | 7 | 57 | 3 | Y | 20/100−2 | 20/50−2 | Y |
| Hyaluro- | 10 | 57 | 4 | N | 20/200 | 20/200+1 | N |
| nic Acid) | 15 | 66 | 4 | N | 20/200 | 20/200 | N |
| | 19 | 60 | 3 | N | 20/100 | 20/300 | N |
| | 20 | 63 | 4 | N | 20/70 | 20/200 | N |
| | 22 | 74 | 4 | Y | 20/200 | 20/200 | N |
| | 25 | 66 | 3 | N | 20/200−1 | 20/200 | N |
| Total Flattened: 3/8 | | | | | | Total Improved: 2/8 | |
| (910 ng) | 3 | 69 | 3 | Y | 20/80+1 | 20/40+1 | Y |
| (With | 4 | 67 | 3 | Y | 20/100−1 | 20/50−2 | Y |
| Hyaluro- | 8 | 58 | 2 | N | 7/200 | CF at 5 ft. | N |
| nic Acid) | 11 | 51 | 4 | N | 20/80 | 20/200 | N |
| | 14 | 76 | 4 | N | 20/200 | 6/200 | N |
| | 17 | 69 | 3 | N | 20/200+1 | 20/400 | N |

TABLE-continued

| Dosage | Patient No. | Age | Stage | Flattening of Edge (Y/N) | Pre-Op | Final | (Y/N) |
|---|---|---|---|---|---|---|---|
| | 21 | 66 | 3 | Y | 20/100−2 | 20/50−1 | Y |
| | 24 | 61 | 3 | N | 20/60 | 5/200 | N |
| | 27 | 74 | 3 | Y | 20/200 | 20/40 | Y |
| | Total Flattened: 4/9 | | | | | Total Improved: 4/9 | |

We claim:

1. A method of improving the ocular vision in retinal disorders of the mammalian eye, said disorders characterized by an insufficiency, loss, or impending loss of fibrous tissue, said method comprising administering to the mammal is eye about 1.1 to 10 µg of transforming growth factor beta (TGF-β).

2. The method of claim 1 wherein the TGF-β is TGF-β2.

3. The method of claim 1 wherein TGF-β is administered by a mode of administration selected from the group consisting of intraocular injection, subretinal injection, subscleral injection, intrachoroidal injection, subconjunctival injection, topical administration, oral administration and parenteral administration.

4. The method of claim 3 wherein the intraocular administration comprises placing TGF-β solution on, under, over, or in the retinal disorder, or any combination thereof.

5. The method of claim 1 further comprising the following steps:
removing the vitreous humor from the eye;
removing the epiretinal membrane, if present; and
administering a concentrated solution of TGF-β by cannula to place the solution immediately over the retinal disorder.

6. The method of claim 1 wherein TGF-β is administered once.

7. The method of claim 1 wherein TGF-β is administered repeatedly until the retinal disorder has ameliorated.

8. The method of claim 1 wherein the dosage of TGF-β is greater than about 100 ng.

9. The method of claim 1 wherein the dosage of TGF-β is greater than 1500 ng.

10. The method of claim 1 wherein the retinal disorder is a macular hole.

11. The method of claim 1 wherein the retinal disorder is macular degeneration.

12. The method of claim 1 wherein the retinal disorder is a retinal tear.

13. The method of claim 1 wherein the retinal disorder is subretinal neovascularization.

14. A method of maintaining or improving the ocular vision in macular degeneration of the mammalian eye, said method comprising administering to said mammal at least 1.1 µg of TGF-β effective to stabilize or improve vision.

15. A method of maintaining or improving the ocular vision in cystoid macular edema, said method comprising administering to said mammal at least 1.1 µg of TGF-β effective to stabilize or improve vision.

16. A method of treating retinal disorders to improve vision, the retinal disorders being characterized by decreased connective or fibrous tissue, said method comprising the following steps:
removing the vitreous humor of the eye;
peeling off the epiretinal membrane, if present; and
administering a dose of a concentrated solution of TGF-β2 by cannula to place the TGF-β2 solution immediately over the portion of the retina requiring treatment, said dose comprising at least 1.1 µg of TGF-β2.

17. A method for treating a mammal with an ophthalmic disorder associated with impaired healing, said method comprising administering orally, locally or systemically, to said mammal a pharmaceutical composition of TGF-β, said composition being administered in an amount sufficient to improve healing in the eye in a dosage range comprising at least 1.1 µg to 10 µg of TGF-β.

18. The method of claim 17 wherein the ophthalmic disorder is selected from the group consisting of retinal edema, retinal wounds, macular degeneration, secondary cataracts, corneal epithelial wounds and Sjögren's syndrome.

19. The method of claim 17 wherein the TGF-β is TGF-β2.

20. The method of claim 19 wherein the TGF-β2 is recombinant human TGF-β2.

21. The method of claim 17 wherein the administration is performed by intraocular, subretinal, subscleral, intrascleral, intrachoroidal injection, or any combination thereof.

22. The method of claim 17 wherein the administration is performed by application to the cornea or sclera.

23. The method of claim 22 wherein the application to the cornea or sclera is placement of a timed release dosage form in the cul de sac.

24. The method of claim 17 wherein the dosage of the pharmaceutical composition is that amount which enhances healing without excessive fibroproliferation.

25. The method of claim 17 wherein the dosage of the pharmaceutical composition is that amount which enhances healing of the ocular condition and improves the mammal's symptoms.

26. The method of claim 17 wherein the dosage of the pharmaceutical composition administered is about 1100 to 5000 nanograms of TGF-β to the eye.

27. A method for treating a mammal that has undergone or is about to undergo or is undergoing ophthalmic surgery to promote healing without excessive scarring, said method comprising administering to said mammal TGF-β, said TGF-β being administered in an amount sufficient to promote healing without excessive scarring in a dosage range of at least 1.1 µg to 10 µg of TGF-β2.

28. The method of claim 27, wherein the TGF-β is administered by direct application in the surgical wound.

29. The method of claim 27, wherein the TGF-β is administered by intraocular, subretinal, subscleral, intrascleral, intrachoroidal injection, or any combination thereof.

30. The method of claim 29, wherein the TGF-β is administered in a solution.

31. The method of claim 29, wherein the TGF-β is administered in a controlled release formulation.

32. The method of claim 27, wherein the TGF-β is TGF-β2.

33. The method of claim 27, wherein the TGF-β2 is recombinant human TGF-β2.

34. The method of claim 27, wherein the ophthalmic surgery is cataract extraction.

35. The method of claim 27, wherein the ophthalmic surgery is corneal transplantation.

36. The method of claim 27, wherein the ophthalmic surgery is glaucoma filtration surgery.

37. The method of claim 27, wherein the ophthalmic surgery is surgery to correct refraction.

38. The method of claim 37, wherein the surgery to correct refraction is radial keratotomy.

39. The method of claim 27 wherein the dosage of the pharmaceutical composition administered is at least about 1100 nanograms of TGF-β per eye.

40. A method of treating a mammal for ocular neovascularization, said method comprising administering to a mammal an effective amount of TGF-β2 in a dosage range of from 1.1 µg to µg of TGF-µ2.

41. The method of claim 40 wherein the TGF-β2 is administered intravenously, topically, intraocularly, intramuscularly, locally or in an ocular device.

42. The method of claim 40 wherein the ocular neovascularization is selected from the group consisting of neovascularization of the cornea, iris, retina, vitreous and choroid.

43. The method of claim 42 wherein the corneal neovascularization is caused by trauma, chemical burns or corneal transplantation.

44. The method of claim 42 wherein the neovascularization of the iris is caused by diabetic retinopathy, vein occlusion, ocular tumor or retinal detachment.

45. The method of claim 42 wherein the retinal neovascularization is caused by diabetic retinopathy, vein occlusion, sickle cell retinopathy, retinopathy of prematurity, retinal detachment, ocular ischemia or trauma.

46. The method of claim 42 wherein the intravitreal neovascularization occurs in diabetic retinopathy, vein occlusion, sickle cell retinopathy, retinopathy of prematurity, retinal detachment, ocular ischemia or trauma.

47. The method of claim 42, wherein the choroidal neovascularization occurs in retinal or subretinal disorders of age-related macular degeneration, presumed ocular histoplasmosis syndrome, myopic degeneration, angioid streaks or ocular trauma.

48. A method of treating uveitis in a mammal, said method comprising injecting intraocularly in said mammal an effective amount of TGF-β2 in a dosage range of at least 1.1 µg to 10 µg of TGF-β2.

* * * * *

UNITED STATES PATENT AND TRADEMARK OFFICE
CERTIFICATE OF CORRECTION

PATENT NO. : 5,767,079
DATED : June 16, 1998
INVENTOR(S) : Bert M. Glaser, Bruce B. Phariss, Ann F. Hanham and George A. Ksander It is certified that error appears in the above-identified patent and that said Letters Patent is hereby corrected as shown below:

At line 4 of claim 1, delete "said" and replace with --the--.

At lines 4-5 of claim 1, delete "mammal is" and replace with --mammal's--.

At line 2 of claim 8, delete "100" and replace with --1100--.

At line 10 of claim 16, insert --to 10 µg-- immediately after "1.1 µg".

At line 4 of claim 40, insert --10-- immediately after "1.1 µg to".

Signed and Sealed this

Thirteenth Day of October 1998

Attest:

BRUCE LEHMAN

*Attesting Officer*  *Commissioner of Patents and Trademarks*